United States Patent [19]
Schrezenmeir

[11] Patent Number: 5,364,346
[45] Date of Patent: Nov. 15, 1994

[54] PROCESS FOR THE CONTINUOUS AND DISCONTINUOUS ADMINISTRATION OF INSULIN TO THE HUMAN BODY

[76] Inventor: Jürgen Schrezenmeir, Backhaushohl 24, 6500 Mainz 1, France

[21] Appl. No.: 210,089

[22] Filed: Mar. 16, 1994

Related U.S. Application Data

[63] Continuation of Ser. No. 931,291, Aug. 17, 1992, abandoned, which is a continuation-in-part of Ser. No. 549,374, Jul. 6, 1990, abandoned, which is a continuation-in-part of Ser. No. 95,534, Oct. 16, 1987, abandoned.

Foreign Application Priority Data

Dec. 20, 1985 [DE] Germany ............................. 3545260

[51] Int. Cl.$^5$ .............................................. A61M 5/00
[52] U.S. Cl. ......................................... 604/50; 604/66
[58] Field of Search ................... 604/50, 66, 189, 207, 604/246

[56] References Cited

U.S. PATENT DOCUMENTS

| | | | |
|---|---|---|---|
| 4,018,223 | 4/1977 | Ethington | 604/207 |
| 4,206,755 | 6/1980 | Klein | 604/50 |
| 4,403,984 | 9/1983 | Ash et al. | 604/50 |
| 4,475,901 | 10/1984 | Kraegen et al. | 604/66 |
| 4,526,568 | 7/1985 | Clemens et al. | 604/50 |
| 4,538,616 | 9/1985 | Rogoff | 604/66 |
| 4,722,734 | 2/1988 | Kolln | 604/246 |

*Primary Examiner*—Ralph A. Lewis
*Attorney, Agent, or Firm*—Edwin D. Schindler

[57] ABSTRACT

A process for the administration of insulin to the human body, particularly the discontinuous administration of insulin to the body, is disclosed. An apparatus for carrying out the process includes either dosing means for metering, or a display for otherwise indicating, the optimum quantity of insulin for a patient. The apparatus permits the measurement of one or more blood sugar levels, compares such blood sugar levels with a series of reference values, and controls the dosing means or display appropriately. In addition, the input data values, as well as the administered amounts of insulin, can be stored and compared with each other over a long period of time and/or evaluated by a computer.

1 Claim, 1 Drawing Sheet

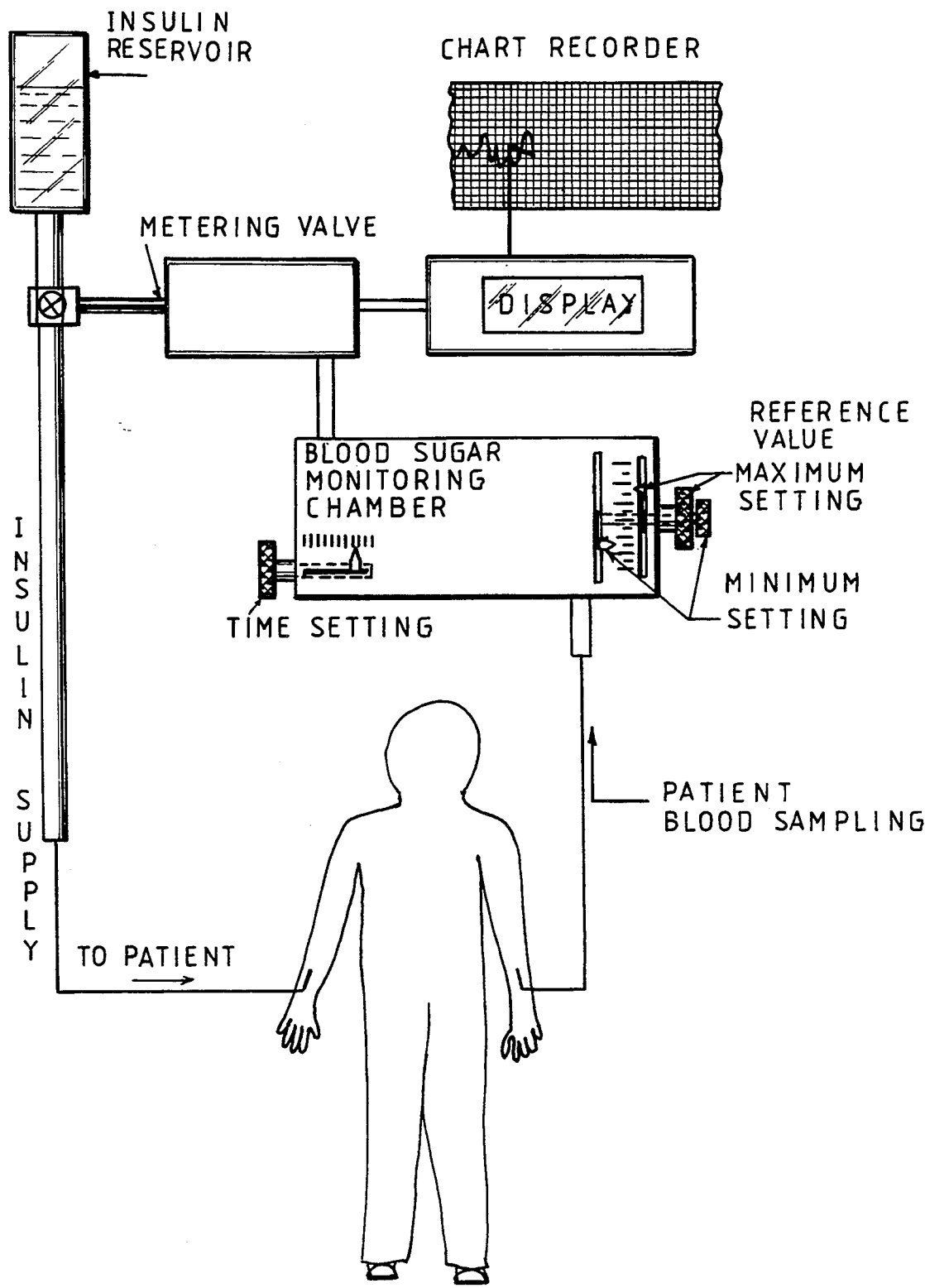

PROCESS FOR THE CONTINUOUS AND DISCONTINUOUS ADMINISTRATION OF INSULIN TO THE HUMAN BODY

CROSS-REFERENCE TO RELATED APPLICATIONS

This application is a continuation of application Ser. No. 07/931,291, filed Aug. 17, 1992, now abandoned, which is a continuation-in-part of application Ser. No. 07/549,374, filed Jul. 6, 1990, now abandoned, which is a continuation-in-part of application Ser. No. 07/095,534, filed Oct. 16, 1987, now abandoned.

BACKGROUND OF THE INVENTION

1. Technical Field of Invention

The present invention relates to an apparatus and process for the administration of insulin to the human body, particularly the discontinuous administration of insulin, which includes dosing means for metering, or a display to indicate, the optimum quantity of insulin.

2. Description the Prior Art

It is generally known in diabetes (diabetes mellitus) that the hormone of the pancreas, i.e., insulin, is either not produced at all or is not produced in a sufficient quantity. If insulin is not available to the body in a sufficient quantity, sugar ingested by the patient with food is not broken down or burned off by the patient's body. In such persons, the sugar concentration in the blood of the person rises and the excess blood sugar is excreted in the person's urine.

As a form of therapy, the diabetic is treated with insulin, either continuously by infusion or discontinuously by injection. In doing so, care is taken to administer the precise amount of insulin lacking in the person's blood. This is carried out by testing and monitoring the patient's blood sugar level. Too small a dose of insulin is just as undesirable as too high an administered quantity, which can lead to dangerous symptoms including, for example, "insulin shock."

The procedure followed, in practice, is to administer to the patient, a certain dose of insulin, which is subsequently changed in dosage on the basis of subsequent reactions, particularly the deviation of the blood sugar level from the reference value, which is carried out by estimation, and is therefore very inexact. In another method known to the art, the optimum dosage of insulin is first determined, with the corresponding quantity thereafter being administered daily. Both methods of dosing produce very inaccurate results because, in the first method described, the determined quantity is inherently inaccurate, while in the latter procedure, the optimum dosage of a patient, usually varies over time and often varies considerably from that originally determined. An additional disadvantageous factor in these methods is that the required quantity of insulin is subject to different, and therefore unpredictable, fluctuations from patient to patient.

Among the prior art known to the inventor, France Patent Application No. 2,387,669, discloses an apparatus, with the aid of which, the blood-sugar value is continuously measured, as well as the optimum quantity to be injected, which is established through comparison with the actual value of the blood-sugar. The proper injection is then immediately given to the patient. With this procedure, one is able to adjust continuously and immediately to the actual values of the patient's condition. The decisive disadvantage of a continuous monitoring procedure, unlike the present invention, is the necessity for stationary institutionalization which robs the patient of the opportunity to lead a normal life.

SUMMARY OF THE INVENTION

It is, therefore, an object of the present invention to provide a process, preferably one which may be utilized on a discontinuous basis, for carrying out a precise quantity administration of insulin to a patient, which overcomes the disadvantages inherent in the prior art.

The foregoing and related objects are accomplished by the present invention wherein a process is disclosed which measures one or more blood sugar levels and compares them with the reference values and the dosing means or a display is controlled according to the results.

An apparatus which may be used in carrying out the present invention would include a control loop that registers one or several blood sugar values as actual values, compares them with reference values and, according to the differences thereby obtained, transmits a control signal to said dosing means or to said display. In this manner, the optimum quantity of insulin is metered. It is therefore possible, on the one hand, to determine the precise requirement of insulin, so that one does not have to resort to estimations or the like, and, on the other hand, fluctuations in requirements can be recognized and taken into account.

The apparatus which is employed for carrying out the claimed process utilizes technology presently known to the prior art in a novel manner. Means for controlling the infusion rates in the administering of insulin is generally known from Kraegen et al., U.S. Pat. No. 4,475,901, issued Oct. 9th, 1984, the relevant portions of which are herein incorporated by reference. Other dosing means generally known to the art are disclosed in Fischell, U.S. Pat. No. 4,731,051, issued Mar. 15th, 1988; and, Ethington, U.S. Pat. No. 4,018,223, issued Apr. 19th, 1977, the disclosures of which are, likewise, incorporated by reference herein. Finally, means for sensing or monitoring the blood sugar levels in patients, relative to the administration of insulin to a patient, is disclosed in Rogoff, U.S. Pat. No. 4,538,616, the disclosure of which is hereby incorporated by reference.

BRIEF DESCRIPTION OF THE DRAWING

In the accompanying drawing FIGURE, a schematic diagram of the claimed process of the present invention, and apparatus for carrying out said process, is presented.

DETAILED DESCRIPTION OF THE DRAWING AND PREFERRED EMBODIMENTS

With reference being made to the accompanying drawing FIGURE, an apparatus for carrying out the process of the present invention includes an input serving to determine the blood sugar level, for example, by removing a small quantity of blood from the patient and feeding it to a device for measurement through the input and either a display or an output, by means of which the quantity of insulin, controlled according to the deviation of the actual blood sugar level from the reference value, is released. The display of the apparatus indicates the quantity that is to be drawn into the syringe.

By means of the present invention, both the continuous and discontinuous administration of insulin is possible, in principle, however, it is preferable that the claimed process be employed in a discontinuous administration of insulin. It is advisable to use the present invention preferably for a discontinuous method, in which, on the one hand, the blood sugar levels are determined, as per conventional means, only occasionally and, on the other hand, the optimum quantities of insulin derived from this are displayed or provided at corresponding time intervals, and then the insulin is dispensed to the patient, preferably by injection. This method of treatment is especially suitable for outpatient treatment and for self-medication by the patient himself.

In a preferred embodiment of the present invention, a plurality of blood sugar levels can be measured at intervals. Such measured data, as well as known amounts of previously administered insulin, can be stored and the control of said means of dosing or said display can be so disposed that, in addition to the deviations from the referenced values, the previously administered amounts of insulin, already introduced into the body, are still active at the time that the blood sugar is measured, is also taken into account when dispensing an additional dose of insulin. On the other hand, with a multiplicity of stored data points, it can be traced as to how the patient has reacted so far to the already administered amounts of insulin, from which conclusions can be drawn about his future behavior so that, by extrapolation, that quantity can be determined which must be administered in order to maintain the reference value in the end effect. Individual modes of behavior by single patients can be recognized and taken into account in future therapy.

It is well known that the blood sugar levels of a diabetic are subject to constant fluctuations on account of external effects. In addition to a base insulin requirement by the pancreas, additional amounts of insulin must be taken upon the consumption of foods in order to burn the carbohydrates contained therein. In practice, long-acting amounts of insulin are often administered to cover the requirement on an empty stomach (i.e., base requirement) and short-acting amounts of insulin for the requirement resulting from meals.

A crucial concept of the present invention is to choose the control of the apparatus so that it allows the exact value of the amount of insulin required for burning the carbohydrate (COH) consumed in food to be determined. The insulin dose IBO (M, I) to be taken on day I for meal M is determined by the product of the carbohydrate (COH(M, I)) and the associated insulin carbohydrate equivalent, ICOHE (M, I). The value of the amount of carbohydrate COH(M, I) fluctuates and is to be determined in dependence on the respective consumed meals, whereby there are no fundamental difficulties involved in determining the consumed quantity of carbohydrate=bread units from the consumption of the meal. Difficulties arise, in principle, however, from the fact that the insulin-COH equivalent ICOHE (M, I) is not only subject to large fluctuations from patient, but takes different values distributed over the day (breakfast, midday and evening meals) in a cyclical manner. One of the crucial concepts of the present invention is to determine the insulin COH equivalent ICOHE (M, I) according to the following method:

Specifically, the insulin dose IBO (M, I) is calculated from the product of the quantity of carbohydrate COH (M, I), taken at meal, M, and the insulin carbohydrate equivalent ICOHE (M, I), resulting from the M-th meal on the Ith day by formula:

$$ICOHE(M, I) = \frac{IBO(M, I-1) - CORI(M, I-1) + CORI(M+1, I-1)}{COH(M, I-1)}$$

wherein,

M is the patient's initial meal;
I is the initially considered day;
IBO (M, I−1) is the corrected insulin dose on the day preceding the M-th meal;
CORI (M, I−1) is the corrected insulin dose on the basis of deviation from the reference carbohydrate level determined from the blood sugar level measured directly before the M-th meal on the previous day using the so-called insulin-blood sugar equivalent;
COH (M, I−1) is the quantity of carbohydrate in the food consumed in the M-th meal on the previous day; and,
CORI (M+1, I−1) is the correcting insulin dose administered on the previous day at the beginning of the (M+1) meal because of the deviation of the blood carbohydrate level from the reference value.

The index, M, here indicates the respective meal, as, for example, breakfast, midday or evening meal. In all likelihood, the food consumption of diabetics is distributed, not over three meals, but usually over 5–6 meals per day. (M+1) designates the following meal. The index, I, designates the presently considered day, hence, (I−1) is the previous day. First, the Insulin dose IBO (M, I−1), administered on the previous day (I−1) at the same meal, M, is stored. From this value is subtracted the corrective amount of insulin, CORI (M, I−1), which corresponds to the portion contained in the insulin dose necessary to compensate for a deficit detected by a blood sugar measurement carried out on the previous day (I−1) before meal M. The value CORI(M, I−1), thus, represents the corrective value for the fact that there was already a blood deficit before consumption of the meal.

To this result, obtained by subtraction, is added the corrective amount of insulin resulting from the fact that on the previous day, (I−1), at the beginning of the (M+1)-th meal a deficit was detected in the blood sugar measurement. This quantity represents a direct indicator of the amount of insulin required for burning the amount of carbohydrate consumed with the M-th meal that would have actually be required.

The result obtained in the foregoing fashion is then divided by the number of bread units consumed in meal, M, on the previous day, (I−1), and indicates the insulin carbohydrate equivalent to be taken as a basis of the calculation for the present, I-th, day at meal, M.

In accordance with the computational method of the present invention, the values for the previous day alone are considered. In a further development, the invention provides for the desired insulin COH equivalent, ICOHE (M, I) on the I-th day at the M-th meal to be computed as an average value from several previous days. The method of determining the average value (e.g., arithmetical, geometrical, etc.) is, in principle, free in this case, in particular, the values determined directly before the day in question could be considered with greater weight in order to take into account the improved adaptation from day to day and, on the other hand, to accelerate the convergence to an ideal value.

The indicated mathematical relationship for computing the insulin dose relates to the insulin doses administered on the previous day and the corresponding blood sugar measurements. This formula is, therefore, unsuitable for determining the insulin dose at the M-th meal on the 1st day, so that one must either refer to previous estimates, or start from the following formula:

$$IBO\ (M,\ I) = \frac{0.45\ DIN}{COH} \cdot b(M)COH(M,\ 1) + CORI(M,\ 1),$$

wherein,
DIN is the daily insulin requirement on previous days;
COH is the overall carbohydrate intake on the same days;
$b(M) = 1.5$ at breakfast; 1.0 at the midday meal; and, 1.2 at the evening meal;
COH(M, I) is the carbohydrate intake on the first day at the M-th meal; and, CORI(M, I) is the correcting dose of insulin on the basis of blood sugar measurement directly before the M-th meal.

The foregoing relationship provides the insulin dose, directly and not, as per the calculations of the prior art, the insulin-COH equivalent.

As a prerequisite, the computation according to the immediately preceding formula requires the previous day's DIN requirement, which is divided by the carbohydrate consumption of the same day. This value, which gives a summary of the complete daily cycle, is first reduced by a factor of 0.45 and increased by the factor b(M), which takes into account the different insulin requirement at each meal corresponding to the daily cycle. The factor b(M) is 1.5 for breakfast; 1.0 for the midday meal; and, 1.2 for the evening meal. This value, obtained by approximation, represents, from the point of view of its dimension, an insulin carbohydrate equivalent that would still have to be multiplied by the quantity of carbohydrates consumed on the first day at the M-th meal (in grams or bread units.) The proportion of the insulin dose that the consumed food covers, or which can be attributed to this food, is then obtained.

The corrective amount of insulin that its still to be administered at the beginning of the M-th meal on the first day owing to the deviation of the blood sugar level from the reference value is then added. The insulin dose to be administered thereby comprises a meal-related proportion—determined by estimation, and a corrective element for adjusting the actual to the reference value.

In the prior art, the computations have referred only to determining the insulin requirements for burning the carbohydrates consumed at meals (in grams or bread units.) An additional proportion of the insulin requirement stems from the requirement on account of the insufficiency of the pancreas. The requirement on an empty stomach is, as a rule, covered by long-acting insulin, that caused consumption of food by short-acting.

To determine the base requirement, the present invention provides that only the blood sugar levels on an empty stomach be considered. This is, for example, the case in the morning, or with administration of short-acting insulin doses after a sufficiently long time interval doses after a sufficiently long time interval, so that no falsification of the measured data is to be expected.

Although the base requirement is to a first approximation approximately constant over the complete day, so that a single data point, e.g., in the morning would be adequate to determine the required value, more exact investigations have shown that the constancy of the base requirement distributed over 24 hours is not exact, but shows relatively constant fluctuations. Thus, the requirement during the night is less than that during the day. In the early hours of the morning, however, the base requirement is at its greatest value. Measurements have further shown that the requirement on an empty stomach changes within 24 hours, i.e., passes through cycles.

The present invention proposes, therefore, that several blood sugar measurements using technology already known to the art (on an empty stomach) be taken during the day, to draw up a base requirement profile from this (=ratio of insulin Infusion rates to each other) with the aid of which the insulin requirement on the following days will be computed in advance.

The determination of the profile is required anew for each patient since it can vary considerably for different patients. Naturally, the values obtained at the beginning of the measurement require correction with respect to the previously administered amounts of insulin that are still in the body.

Further adjustment of the insulin requirement on an empty stomach—maintaining the ratio of the insulin infusion rates to each other—is then done taking into account the current measured blood sugar levels on an empty stomach.

To determine the base requirement, the proportion required for burning carbohydrates is then added, calculated, for example, by the formula given above.

Determination of the blood sugar level requires constant extraction and analysis of quantities of blood, as per the prior art incorporated by reference into this disclosure. This measuring method is elaborate and not satisfactory for the out-patient treatment of diabetics.

Another important concept of the present invention, therefore, includes the determination of the blood sugar levels by measurement of the urine sugar. This is possible because, with the aid of a conversion factor, the so-called urine/blood sugar equivalent, the associated blood sugar can be theoretically calculated with a reasonable degree of accuracy from the measured value for the urine sugar. This requires the simultaneous measurement both of the urine and blood sugar over a certain period of time, from which the necessary urine/blood sugar equivalent can be determined specific to the patient and individually. The measurement of the urine sugar is much simpler, less problematical, and can be done easily by each patient himself. This type of indirect measurement of the blood sugar, however, is not suitable for slightly elevated blood sugar levels, since then the kidney threshold has not been reached and no sugar is excreted in urine. It will generally be the rule that the change of blood sugar level, after consumption of a meal, will have exceeded this level, at least partially, so that at least during these phases, the concept of the invention can be realized.

Further possibilities for its employment are produced by the use of a computer in conjunction with control of said dosing means; means which are generally known to the prior art and referenced herein. This is useful and employable in many respects. The decay of the action of already administered insulin can be input into the computer and be so taken into account exactly in the subsequent measurements taken during any desired time thereafter.

Another, further possibility, independent thereof, is to input the changing insulin requirement according to the day-night cycle by suitable programming, so that this effect enters into this computation.

Finally, the possibility is further provided, to input already known, or still to be developed, formulae into the computer, with the aid of which, using the measured blood sugar values, a further improvement of the insulin dose to be determined, is possible.

In addition to the intake of carbohydrates, for example, in foods, it is known that the required insulin dose is changed, as well, by physical activities. The effects caused thereby can be estimated and, as provided in a further development of the present invention, be taken into account by means of an input acting, in effect, on the control of the dosage, so that the released insulin dose is increased (or reduced) accordingly. The changes of the insulin dose occurring through external effects, deviating from the usual cycle, can thereby be taken into account in the measurement of the optimum insulin dosage.

The present invention makes available a device, with the aid of which a precise metering of the insulin dose required by the patient is possible.

While only several embodiments of the present invention have been shown or described, it will be obvious to those of ordinary skill in the art that many modifications may be made to the present invention without departing from the spirit or scope thereof.

What is claimed is:

1. A process for the administration of insulin to a patient based upon a determination of a blood carbohydrate level of the patient, comprising the steps of:
   (a) administering an initial series of dosages of insulin to the patient;
   (b) measuring the blood carbohydrate level of the patient during said administering step;
   (c) recording and storing the blood carbohydrate levels obtained during said measuring step;
   (d) determining a new quantity of insulin to be administered based upon an insulin carbohydrate equivalent level of the patient obtained in said measuring step in accordance with the formula:

$$ICOHE(M, I) = \frac{IBO(M, I-1) - CORI(M, I-1) + CORI(M+1, I-1)}{COH(M, I-1)}$$

wherein,

M is the patient's initial meal;

I is the initially considered day;

IBO (M, I−1) is the corrected insulin dose on the day preceding the M-th meal, so that the IBO (M, I−1) value is the quantity of insulin administered to the patient at meal M on a preceding day I−1;

CORI (M, I−1) is the corrected insulin dose on the basis of deviation from a reference carbohydrate level determined from a blood sugar level measured directly before the M-th meal on the previous day using an insulin-blood sugar equivalent so that the CORI (M, I−1) value is the product of said insulin-blood sugar equivalent and the difference between the blood sugar level and the reference carbohydrate level, with the reference carbohydrate level being an optimal blood sugar level for the patient necessary for determining the initial insulin dose, and the insulin-blood sugar equivalent being the quotient of a value of insulin given to the patient and a resulting change in the blood sugar level of the patient;

COH (M, I−1) is the quantity of carbohydrate in the food consumed in the M-th meal on the previous day; and, CORI (M+1, I−1) is the correcting insulin dose administered on the previous day at the beginning of the (M+1) meal because of the deviation of the blood carbohydrate level from the reference value, so that a quantity of insulin IBO (M, I), at meal M and day I is determined from the product COH (M, I) and the insulin carbohydrate equivalent level ICOHE (M, I), with COH being the quantity of carbohydrate in food consumed in the meal M on the day I;

and, (e) administering to the patient the new quantity of insulin, as determined by the insulin carbohydrate equivalent level in said determining step, based upon a desired insulin per unit of carbohydrate for the blood of the patient following treatment.

* * * * *